United States Patent [19]

Marshall et al.

[11] Patent Number: 4,504,493

[45] Date of Patent: Mar. 12, 1985

[54] SOLUTION FOR SURGICAL IRRIGATION

[75] Inventors: G. June Marshall, Los Angeles, Calif.; Stephen J. Snyder, 19525 Shirley Ct., Tarzana, Calif. 91356

[73] Assignee: University of Southern California by G. June Marshall, Los Angeles, Calif. ; a part interest

[21] Appl. No.: 514,224

[22] Filed: Jul. 15, 1983

[51] Int. Cl.³ .......................................... A61K 31/045
[52] U.S. Cl. .................................................. 514/738
[58] Field of Search ...................................... 424/343

[56] References Cited

U.S. PATENT DOCUMENTS

| | | | |
|---|---|---|---|
| 2,583,576 | 1/1952 | Kern et al. | 167/81 |
| 2,721,825 | 10/1955 | Hardie | 167/50 |
| 3,356,575 | 12/1967 | Arbaceus et al. | 167/95 |
| 3,422,186 | 1/1969 | Sasmor | 424/79 |
| 3,481,334 | 12/1969 | Diskin | 128/230 |
| 4,168,700 | 9/1979 | Opelt et al. | 128/630 |

OTHER PUBLICATIONS

Husa's Pharmaceutical Dispensing, (1966), Sixth Edition, Mack Publishing Company, Easton, Penna., p. 191.
Handbook on Nonprescription Drugs, 1977, American Pharmaceutical Association, Wash., D.C., pp. 232 & 234.
Brian F. Reagan, et al., "Irrigating Solutions for Arthroscopy," 65-A, *The Journal of Bone and Joint Surgery, Incorporated*, No. 5, (Jun. 1983), pp. 629-631.
Gerald P. Murphy, "A New Isotonic Irrigating Solution for Use in Transurethral Surgery," 100, *The Journal of Urology*, (1968), pp. 88-89.
Thomas G. Johans, M.D. et al., (Letter to Editor), "Hyperlactatemia During Transurethral Resection of the Prostate Using Sorbitol Solution as the Urologic Irrigant," 52, *Anesthesiology*, (1980), pp. 374-375.
P. Bruhl, et al., "Pyrogenfreies Sterilwasser fur die Transurethrale Operative Endoskopie," 32, *Urol. Int.*, (1977), pp. 18-24.
von Dr. F. Hieber, Landau, "Erfolge mit Enelbin bei Arthrotischen und Praearthrotischen Beschwerden des Kniegelenks," 21, Jahrgang, *Med. Mschr.*, (1967), pp. 231-232.
Edward Hitchcock, "Hypothermic Subarachnoid Irrigation for Intractable Pain," *The Lancet*, (May 27, 1967), pp. 1133-1135.
R. M. Maher, "Relief of Pain in Incurable Cancer," *The Lancet*, (Jan. 1, 1955), p. 18.
James M. Fox, M.D., *Arthroscopic Subcutaneous Lateral Release A New Technique*, Electrosurgery-Concept, Inc. (1982).
G. Klaud Miller, et al., "The Use of Electrosurgery for Arthroscopic Subcutaneous Lateral Release", *Arthroscopic Subcutaneous Lateral Release a New Technique*, (1982), p. 312, First Full Paragraph.

*Primary Examiner*—Frederick E. Waddell
*Attorney, Agent, or Firm*—Nilsson, Robbins, Dalgarn, Berliner, Carson & Wurst

[57] ABSTRACT

An isomolar solution of glycerol and water containing glycerol in the amount of about 2.75 weight percent is provided as a non-cytotoxic, non-hemolytic, non-viscid, non-conductive and optically clear surgical irrigation solution.

7 Claims, 8 Drawing Figures

SOLUTION FOR SURGICAL IRRIGATION

FIELD OF THE INVENTION

This invention relates to the field of the medical sciences and, in particular, relates to irrigation fluids for use in arthroscopic surgery and other surgical manipulations where continuous irrigation is employed.

BACKGROUND AND SUMMARY OF THE INVENTION

Certain forms of surgery require irrigation fluids to clean or distend a body cavity or portion. For example, cystoscopy and endoscopic transurethral prostatectomy require the continuous irrigation of the body cavity through the endoscope. In addition, electro-surgical procedures often require continuous irrigation of the body portion which comprises the operative field.

Arthroscopy is a procedure by which a joint, e.g., elbow, ankle or knee is visually examined with an arthro-endoscope, which may include a lens system to enable direct visual examination of the joint or a fiberoptic probe which may be linked to electronic imaging devices. Such tools have long been used as instruments for the diagnosis of various joint ailments.

Arthroscopic surgery is an extension of diagnostic arthroscopy, and early successes include the biopsy of the synovial membrane and medial menisectomy. More recently, specialized arthroscopic instruments and surgical techniques have been developed. It is now common to use motorized instruments to aid in the trimming of the meniscal rim as well as the articular cartilage. In addition, electro-surgical techniques have been developed which enable the precise cutting, separation or coaptation of various tissues, or the coagulation of coaptation of localized vasculature.

Irrigation fluids have long been employed to distend body portions which are endoscopically examined or treated. For example, distention of the knee joint is required in order to allow the insertion of the endoscopic instrument therein. In addition, arthroscopic surgical procedures require continuous irrigation to remove surgical debris. For example, motorized instruments require large volumes of irrigation fluid, i.e., up to 10-12 liters when synovial resection or meniscal surgery is performed.

Irrigation fluids, whether used for arthroscopy or other endoscopic operations such as urethral recsetomy, are selected according to rigid requirements. The irrigant must be isotonic (i.e. isosmotic: exerting the same osmotic pressure as ambient body fluids), non-viscous, non-antigenic and non-toxic. In addition, it should be easily sterilizable and optically clear. In addition, it would be advantageous for the irrigant to have a long shelf life in a concentrated form and be substantially inexpensive.

Various forms of irrigating fluids have been employed. Sterile water has been used for a number of years by various arthroscopists as distilled water is substantially non-conductive, and thus the high potentials required by electrosurgery may be employed without effecting either the patient or the surgeon. However, water is hemolytic and hypotonic and thus tends to add fluids to the surrounding tissue and extract hemoglobin from blood cells, with concomitant damage thereto. For example, hypotonic water solutions may cause water intoxication which leads to disruption of the central nervous system and can result in nausea, somnolence and even death. Isotonic salt solutions such as normal saline have also been used, as such solutions are readily available and are known to have relatively physiological osmotic properties. However, normal saline has a pH of about 5.0, well below the body pH of about 7.4. When large volumes of irrigant are necessary for extended arthroscopic surgery, the physiology of the surgical area may be significantly altered due to this pH difference. Moreover, ionic salt solutions are obviously unsatisfactory for electro-surgery because of their conductivity.

Various non-ionic solutions have been enployed, but have presented additional problems. For example, while isotonic, sugar solutions have been found to be viscous and sticky and are thus unpleasant for the surgical staff. Sugar solutions also cause visual disturbances when in motion, and when concentrated sugar solutions are sterilized by heat they develop an objectional color which affects the endoscopic viewing field. The sugar solutions generally available include sorbitol, manitol and combinations thereof. The use of urea or other non-ionic salt solutions has also been attempted and such solutions present certain advantages with regard to optical clarity. However, urea hemolyzes red blood cells and is therefore as dangerous, if not more so, than water. Protein based mixtures such as albumin solutions produce undesired antigenic responses which may disrupt the entire immunologic system and, as they are derived from blood sources, are unreasonably expensive.

A currently accepted irrigating solution is an isotonic solution of glycine (aminoaecetic acid, $NH_2CH_2COOH$). While glycine solutions offer some advantages, it has some conductivity and has a solubility that is below that necessary to allow the preparation of an aqueous concentrate. In addition, glycine solutions have a pH below that of normal body fluids, tend to cause protein coagulation and tend to precipitate when exposed to the high temperatures at the tip of the electro-surgical probe. Moreover, glycine solutions are absorbed by the body and may be toxic, and glycine is substantially more expensive than many of the alternatives heretofore described.

Accordingly, it has been a desideratum to provide an irrigating solution for endoscopic diagnosis and surgery which is isotonic, non-viscous, non-precipitating at the temperatures occasioned by such surgery, non-antigenic, and non-toxic; which is optically clear at high magnification, is inexpensive and doesn't alter the body chemistry of the treated portion; and which is easily sterilizable and capable of being distributed as a concentrated solution precursor having a long shelf life.

We have discovered a surgical irrigation solution which overcomes the foregoing problems, and provides additional advantages over solutions presently known. The irrigation solution of the present invention is optically clear at extreme magnification and is non-electrolytic so as to allow its use in any form of endoscopic examination or surgery. It is non-antigenic, non-toxic and is isotonic such that it does not alter body chemistry or affect the viability of body cells in the operative area. The solution of the present invention is inexpensive and is not viscous or sticky, so that it may be used in substantial amounts and without the discomfort heretofore present in the use of non-electrolytic sugar-based irrigating solutions. The solution is also easily sterilizable and may be stored in concentrated form for extended periods.

According to the present invention, a surgical irrigation solution is provided which comprises a 2% to 3.5% glycerine-water solution which is substantially isotonic, having an osmolality of from about 200 to about 350 milliosmoles. Preferably, the solution contains glycerine in an amount of from 2.8 to 3.0% and thus having an osmolality of from 280 to 300 milliosmoles.

DETAILED DESCRIPTION

Figure 1:
FIG. 1 is a photomicrograph of a normal synovial surface.

In the preferred embodiment hereinafter set forth, the present invention will be described with respect to arthroscopic knee surgery, i.e. perfusing a knee joint with an irrigating solution and releasing the lateral patellar retinaculum with a radio frequency cutting current. The effect of the irrigating solutions on the articular hyaline cartilage and synovium was determined immediately after irrigation and after a period of 3 to 4 weeks recovery from the irrigation. The synovium and cartilage were studied for gross, light microscopic and electron microscopic changes. However, it is to be understood that this embodiment merely exemplifies the invention, but may be applied to other methods and types of surgery with similar benefits. Therefore, specific functional details are not necessarily to be interpreted as limiting, but rather as a basis for the claims.

The strength of the solutions employed in the examples hereinafter set forth is described in terms of osmolarity, i.e., the molar concentration of the solution. For convenience, this strength is described in terms of milliosmolarity (mOsm, osmolarity/1000), as the osmolarity of normal body fluids is known to be in the range of 290-310 mOsm. In particular, glycerol (1, 2, 3-propane triol), with a molecular weight of 92.1 forms a solution having an osmolarity of 1 mOsm when added to water in the amount of $9.21 \times 10^{-2}$ gm/L. Consequently, a 300 mOsm glycerol solution is formed by the addition of 27.63 grams of glycerol to 1 liter of water, i.e., 2.763 weight percent. Using such calculated osmolarities, solutions of approximate strength may be prepared. However, as the purity of the solute may vary, it is preferable to employ a standardized osmometer to ensure exact solution concentration. With regard to glycerol, it has been determined that 27.5 grams/L provides a glycerol-water solution having an osmolarity of 300 mOsm.

EXAMPLE I

Animal studies were undertaken wherein the effects of the irrigating solution of the present invention and other irrigating solutions on the articular hyaline cartilage and synovium was assessed. In this study these structures were studies for gross, light microscopic and electron microscopic changes, both immediately after irrigating and after a period of three to four weeks' recovery from the irrigation. The results of this study relate directly to the acute and chronic damage to the synovia and articular cartilage to the human knee joint when performing a lateral retinaculum via an arthroscope.

Ten-week old male New Zealand white rabbits were anaesthetized intravenously with sodium pentabarbital, 2.5 mgm per kg. All animal surgery was performed under strict aseptic conditions. The knee was shaved up to the inguinal area and down to the midshaft of the tibia and the skin washed with betadine scrub solution. For each surgical procedure both knees were prepped and draped and the animal was covered with sterile towels. An eighteen guage needle was inserted into the medial aspect of the suprapatellar pouch and a second eighteen guage needle was inserted into the anterior aspect of the knee. The accurate positioning of the needles was tested by a brief flow of the irrigation solution for five minutes. If the flow was appropriate, as indicated by the absence of subcutaneous accumulation of fluid, the flow was continued for an additional fifteen minutes. At the end of the twenty minute perfusion, the animals were immediately sacrificed and the patella, synovium and cartilages were removed, bisected and placed into a fixative, i.e., 10% buffered formaldehyde for routine sections and 5% gluteraldehyde in 0.1m cacodylate buffer (pH 7.2) for electron microscope studies. Prior to the removal of the tissue, the knees were evaluated for gross anatomy to ascertain if any dramatic changes had occurred during the course of the irrigation. A summary of this perfusion data is shown in Table I.

Other rabbits were perfused in a similar manner, but were allowed to fully recover from anaesthesia and return to their respective cages so that the long term effect of the perfusion could be determined. After three to four weeks these animals were sacrificed and the knees examined as described above with regard to the determination of acute perfusion damage. Perfusion data with regard to the animals tested for long term damage is shown in Table II.

EXAMPLE II

Tracer studies in knee joints were undertaken to ascertain if various irrigation fluids caused a rapid movement of molecules across the surface of the synovium, i.e., if the synovium sustained damage from the irrigation fluid and allowed the diffusion of large molecules. The diffusion tags employed were glycogen and ferritin. An initial experiment was done with two knees from one rabbit to ascertain if the tags could be detected. Following this pilot study, four rabbits were prepared for knee irrigation as described above. Surgical water, surgical saline and an isomolar glycerol solution were used as irrigating fluids. Each of these fluids were perfused for 20 minutes into the designated knees and at the end of this time 100 mg ferritin and 200 mg glycogen were perfused for four minutes. Thereafter, the knees were washed by the primary perfusion fluid.

Euthanasia was immediate by an overdose of sodium pentobarbital. The knees were removed and bisected. One half of each knee was placed in absolute methanol for fixation and light microscopy histochemistry studies. The other half were fixed in 5% gluteraldehyde and 1.1M cacodylate buffer, pH 7.2, for transmission electron microscopy. Data with regard to the irrigation fluids used in this diffusion study is given in Table III.

In reviewing the photomicrographs of the joints obtained as described in Example One it was was noted that the greatest cellular damage was induced by surgical water, due primarily to the hypo-osmolarity of this irrigating solution. In a similar manner, the hypotonic glycerol-water solution also produced cell damage. Synovial lining and cartilage obtained when the joints were irrigated with isotonic glycerol-water solutions were comparable in morphology to the normal synovia and articular cartilage controls.

Figure 2:
FIGS. 2 and 3 are photomicrographs of a synovial surface after acute irrigation with surgical water.
Figure 3:
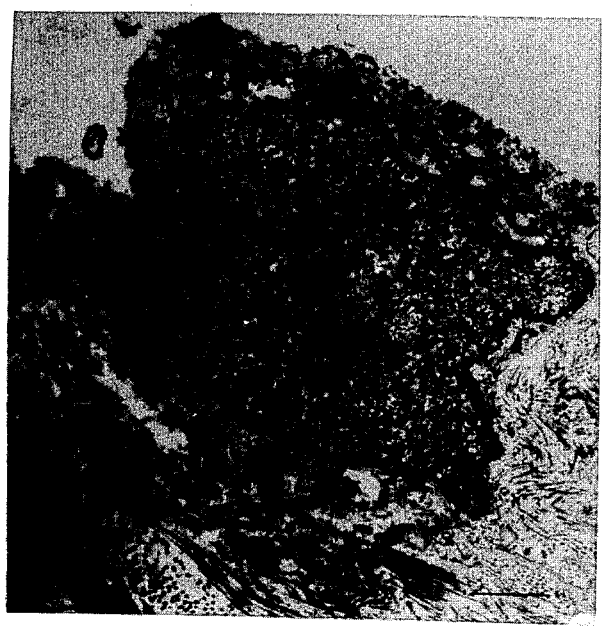

A normal synovial surface is shown in FIG. 1 with portions of several cells. The cell with the nucleus is a Type A cell with minimal synthetic activity as reflected by the rough endoplasmic reticulum. The cytoplasmic and nuclear membranes are intact. One can easily note the loose association of synovial cells to one another. The underlying blood vessel is normal and is associated with a pericyte. Sections through cell processes from Type B synthetic cells are indicated by arrows. FIG. 2 shows the synovial surface immediately after irrigation with surgical water, and shows a loss of cellular integrity. Cell membranes are not resolved, the nuclei are swollen with a loss of chromatin pattern (C) and organelles are difficult to delineate. FIG. 3 details further damage to the synovial lining by irrigation with water. The cell integrity is gone, the nucleus is swollen and the organelles are diminished and injured.

The cellular changes which resulted from irrigation with hypotonic glycerol-water solutions were comparable to the cellular changes seen with water. Photomicrographs of the joints employed to determine chronic damage, as described in Table II, also showed damage from hypotonic osmolarity e.g. the cells were cracked and appeared to be markedly more fragile than in untreated joints. Joints irrigated with the hypotonic sorbitol and glycine solutions also showed cell damage similar to that of the hypotonic glycerol-water solution. In this regard the hypotonic glycerol, sorbitol and glycine solutions, having an osmolarity of from about 80 to about 195, do not show cytoplasmic changes as severe as those shown with water in that the cell membrane is intact in some cells and the organelle dislocation is minimal. However, the nuclear changes are comparable to those which result from surgical water irrigation.

Figure 4:
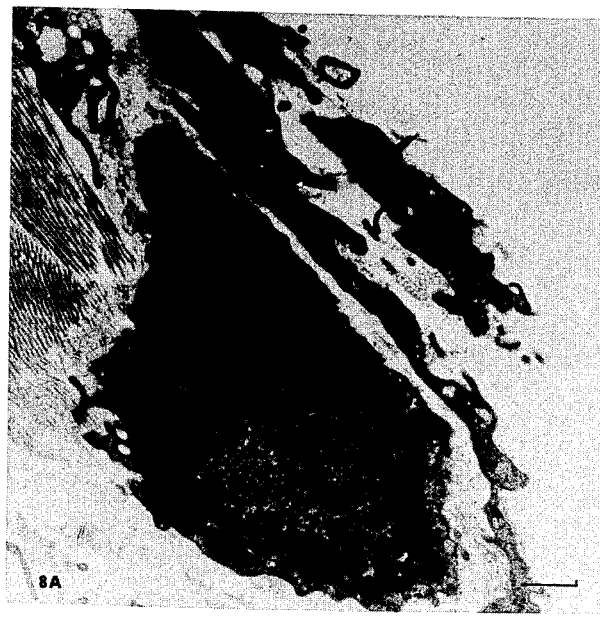
FIGS. 4-7 are photomicrographs of synovial lining cells after acute exposure to the isotonic glycerol-water irrigating solution.
Figure 5:
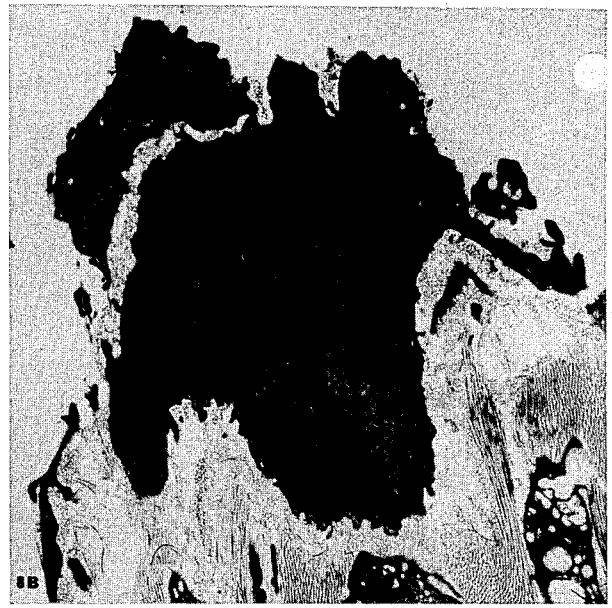

FIGS. 4–7 show photographs of synovial cells after acute exposure to an isotonic glycerol-water irrigating solution. FIG. 4 shows a synovial lining cell with a large nucleus and normal cytoplasm. The rough endoplasmic reticulum (rER), mitochondria (M), and occasional lysosomes (L) are present. Processes of other lining cells are noted at S. Collagen (Co) is present and normal. FIG. 5 shows a synthetically active synovial cell with a high concentration of mitrochondria (M) and rER. The cell membrane is intact and no loss of cell integrity is noted.

Figure 6:
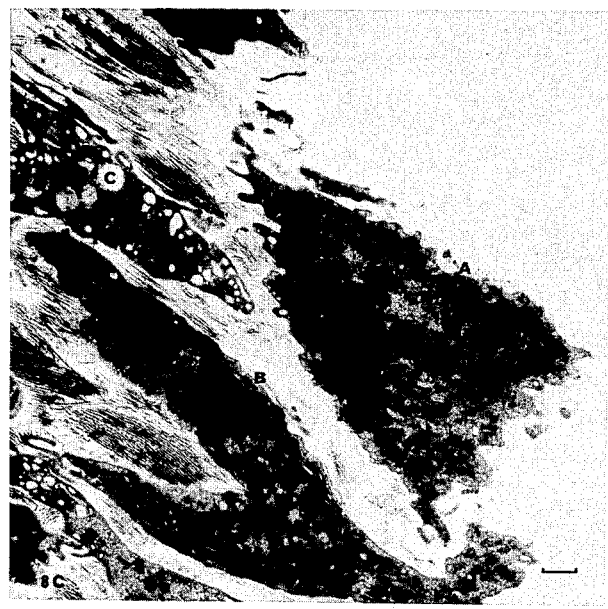
Figure 7:
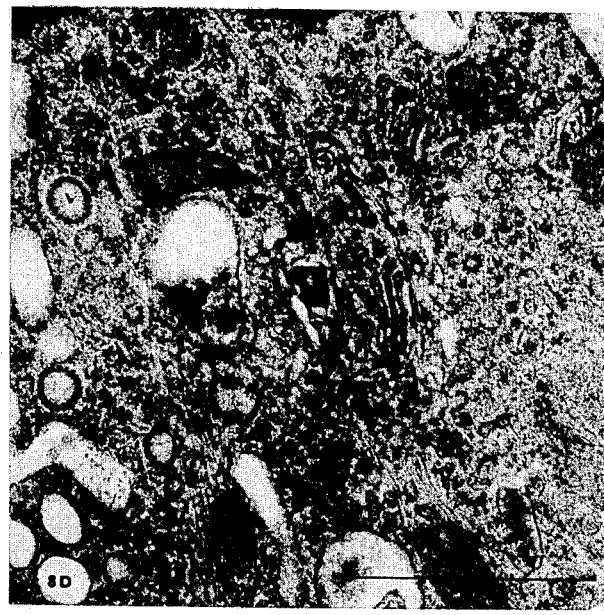

FIG. 6 also shows synovial lining cells with normal morphology. The cell at A is Type A and contains lysosomes (L) whereas the cell labelled B is a Type B synthetic synovial cell. The Type A cell designated C has a high concentration of pinocytotic vesicles and vacuoles. This type of variation is often seen in normal synovia. FIG. 7 shows an area of synovial cell which highlights the Golgi complex (G), filaments (F), vesicles (V) and ribosomes (r) which are seen in normal synovia.

Figure 8:
FIG. 8 is a photomicrograph of a synovial lining cell after chronic exposure to the isotonic glycerol-water solution.

FIG. 8 shows a photomicrograph of a synovial lining cell after chronic exposure to the isotonic glycerol-water irrigation solution, and demonstrating normal morphology as well as nuclear and cytoplasmic plasmic integrity.

The lining cells of the joints perfused with glycine, mannitol and sorbitol appeared to be less swollen than those irrigated with water, although some of the glycine-irrigated cells exhibited very large vacuoles. The changes in the synovial lining after perfusion with mannitol and sorbitol produced varied morphological changes including cells with swollen nuclei and disrupted membranes, cells with edematous nuclei but with cell membranes intact, and cells with little or no changes.

In summary, the described examples indicate that the isotonic glycenol-water solution causes no damage to body cells in the irrigated area.

From the foregoing description, one skilled in the art can readily ascertain the essential characteristics of the invention as well as the advantages of the isotonic surgical irrigation solution disclosed herein and, without departing from the spirit and scope thereof, can adapt the invention to various usages and conditions. Changes in form and the substitution of equivalents are contemplated as circumstances may suggest or render expedient; and although specific terms have been employed herein, they are intended in a descriptive sense and not for purposes of limitation, the purview of the invention being delineated in the following claims.

TABLE I

| Irrigation Fluid | n | Perfused Amount ± S.D. | pH | Osmolarity (mOsm) |
|---|---|---|---|---|
| glycerol (isomolar) | 22 | 114 ± 54 | 7.0 | 301 |
| glycerol hypotonic | 8 | 64 ± 48 | 6.2 | 82 |
| water | 13 | 108 ± 44 | 6.8 | 2 |
| surgical saline | 12 | 127 ± 53 | 5.3 | 281 |
| balanced saline | 10 | 153 ± 45 | 7.2 | 275 |
| sorbitol | 3 | 142 ± 19 | 5.2 | 180 |
| mannitol | 3 | 164 ± 23 | 5.4 | 287 |
| glycine | 3 | 158 ± 14 | 6.1 | 193 |
| albumin | 7 | 141 ± 41 | 6.6 | 271 |

TABLE II

| Irrigation Fluid | n | Perfused Amount ± S.D. | pH | Osmolarity (mOsm) |
|---|---|---|---|---|
| glycerol isomolar | 5 | 100 ± 33 | 7.0 | 300 |
| water | 6 | 140 ± 65 | 6.8 | 2 |
| surgical saline | 7 | 155 ± 73 | 5.3 | 282 |
| balanced saline | 9 | 99 ± 26 | 7.1 | 278 |
| sorbitol | 4 | 167 ± 29 | 5.2 | 180 |
| mannitol | 3 | 145 ± 48 | 5.4 | 287 |
| glycine | 3 | 178 ± 89 | 6.1 | 193 |
| albumin | 6 | 120 ± 54 | 6.6 | 271 |

TABLE III

| ANIMAL # AND KNEE | IRRIGATION FLUID | DIFFUSION TAG | OSMOLARITY | AMOUNT OF IRRIGATION |
|---|---|---|---|---|
| INITIAL PILOT | | | | |
| 37R | Surgical Saline | 100 mg ferritin 750 mg glycogen | 298 | 140 ml |
| 375L | Surgical Saline | 750 mg glycogen | 298 | 58 ml |
| EXPERIMENT | | | | |

TABLE III-continued

| ANIMAL # AND KNEE | IRRIGATION FLUID | DIFFUSION TAG | OSMOLARITY | AMOUNT OF IRRIGATION |
| --- | --- | --- | --- | --- |
| 376R | Surgical Saline | 100 mg ferritin<br>200 mg glycogen | 298 | 70 ml |
| 377R | Surgical Water | 100 mg ferritin<br>200 mg glycogen | 0-1 | 118 ml |
| 378R | Glycerol | 100 mg ferritin<br>200 mg glycogen | 298 | 125 ml |
| 379R | Glycerol | 100 mg ferritin<br>200 mg glycogen | 298 | 133 ml |
| 379L | Surgical Water | 100 mg ferritin<br>200 mg glycogen | 0-1 | 175 ml |
| 380R | Glycerol | 100 mg ferritin<br>200 mg glycogen | 302 | 52 ml |
| 380L | Surgical Saline | 100 mg ferritin<br>200 mg glycogen | 280 | 78 ml |

We claim:

1. In a method of performing surgery on a body portion, the step of irrigating the surgical field with an essentially isotonic, non-electrolytic and optically clear solution of glycerol and water.

2. The method of claim 1 wherein the solution contains glycerol in the amount of about 2.75 percent by weight.

3. The method of claim 1 or 2 wherein the surgery is arthroscopic electrosurgery and the surgical field is the knee.

4. The method of claim 1 or 2 wherein the surgery is urological or gynecological surgery.

5. The method of claim 1 or 2 wherein the solution consists essentially of glycerol and water.

6. The method of claim 3 wherein the solution consists essentially of glycerol and water.

7. The method of claim 4 wherein the solution consists essentially of glycerol and water.

* * * * *

UNITED STATES PATENT AND TRADEMARK OFFICE
CERTIFICATE OF CORRECTION

PATENT NO. : 4,504,493
DATED : March 12, 1985
INVENTOR(S) : G. June Marshall and Stephen J. Snyder It is certified that error appears in the above-identified patent and that said Letters Patent are hereby corrected as shown below:

Column 4, Lines 14 and 16, "guage" should be --gauge--

Column 6, Line 18, "membrances" should be --membranes--.

Signed and Sealed this

Ninth Day of July 1985

[SEAL]

Attest:

DONALD J. QUIGG

Attesting Officer     Acting Commissioner of Patents and Trademarks